United States Patent [19]

Katzir et al.

[11] Patent Number: 5,153,668
[45] Date of Patent: Oct. 6, 1992

[54] OPTICAL INSPECTION APPARATUS AND ILLUMINATION SYSTEM PARTICULARLY USEFUL THEREIN

[75] Inventors: Yigal Katzir, Holon; Oded Arnon, Givatayim; Eyal Teichman, Rehovot, all of Israel

[73] Assignee: Orbot Systems Ltd., Yavne, Israel

[21] Appl. No.: 696,740

[22] Filed: May 7, 1991

[30] Foreign Application Priority Data

May 11, 1990 [IL] Israel .................................. 94368

[51] Int. Cl.[5] ........................................... G01N 21/17
[52] U.S. Cl. ................................................. 356/237
[58] Field of Search ............... 356/394, 237; 358/106

[56] References Cited

U.S. PATENT DOCUMENTS

| | | | |
|---|---|---|---|
| 2,257,881 | 10/1941 | Jaros . | |
| 3,806,256 | 4/1974 | Ishak | 356/186 |
| 3,825,322 | 7/1974 | Mast | 350/236 |
| 4,319,847 | 3/1982 | Howarth | 356/431 |
| 4,320,442 | 3/1982 | McCamy | 362/301 |
| 4,421,410 | 12/1983 | Karasaki | 356/378 |
| 4,423,470 | 12/1983 | Naito et al. | 362/17 |
| 4,449,818 | 5/1984 | Yamaguchi et al. | 356/237 |
| 4,816,686 | 3/1989 | Hara et al. | 356/237 |
| 4,881,802 | 11/1989 | Stankewitz | 350/525 |

FOREIGN PATENT DOCUMENTS 2142444 1/1985 United Kingdom .

OTHER PUBLICATIONS

Goodman, "Illuminator for Dark Field Microscopy", Aug. 15, 1984 Applied Physics pp. 2670-2671.
Goodman, "Illuminators Based on Fiber Rings" Jun. 1, 1985 Applied Physics pp. 1560-1561.

Primary Examiner—Richard A. Rosenberger
Attorney, Agent, or Firm—Benjamin J. Barish

[57] ABSTRACT

Optical inspection apparatus includes an illumination system illuminating an area of the workpiece surface with a sky of illumination which is, with respect to each point in the illuminated area, substantially circularly symmetric over a solid angle around the optical axis passing perpendicularly through the electro-optical sensor and the workpiece surface.

18 Claims, 4 Drawing Sheets

OPTICAL INSPECTION APPARATUS AND ILLUMINATION SYSTEM PARTICULARLY USEFUL THEREIN

BACKGROUND OF THE INVENTION

The present invention relates to inspection apparatus for optically inspecting the surface of a workpiece, and also to a surface illumination system which is particularly useful in such inspection apparatus. The invention is especially useful in the high speed, automated, optical inspection of printed circuit boards, wafers and the like, for detecting faults which require reworking, and therefore the invention is described below with respect to this application; it will be appreciated, however, that the invention, or features thereof, could advantageously be used in other applications as well.

The conventional inspection apparatus for optically inspecting the surface of a workpiece, such as a printed circuit board or wafer, in order to detect faults, typically includes a memory for storing reference data relating to the desired features of the workpiece surface, an illumination system for illuminating the workpiece surface, an optical sensor for sensing the light reflected from the illuminated workpiece surface and for outputting electric signals corresponding thereto, and a processor including logic circuitry for analyzing the electric signals outputted by the optical sensor for comparing them with the data stored in the memory, and for providing an indication of any discrepancies with respect thereto indicating a defect in the inspected workpiece surface. The reference data, concerning the desired features of the workpiece surface to be compared with the sensed workpiece surface, may relate to stored images of the desired workpiece surface, or to stored design rules for the design of such workpiece surface.

Since the workpiece surfaces are not perfectly flat, but rather exhibit some degree of surface relief such as grooves, scratches, and angled surfaces, it would be desirable that the illumination system include a Lambertian diffuser, namely a perfect diffuser effective to cause the intensity of reflected radiation to be indepedent of direction. Such illumination would produce spatial uniformity of the light (i.e. a uniform "sky of illumination") above the workpiece and thereby eliminate shadows caused by the relief in the workpiece surface. However, Lambertian diffusers are extremely wasteful of light, and therefore such a diffusing surface would require an extremely intense light source and extremely high power, or would substantially slow the operation of the inspection apparatus in order to obtain workable signals having the required signal-to-noise ratio.

The existing optical-inspection systems therefore provide focussed "Quasi-Lambertian" illumination. Examples of such illumination systems are described in our prior Israel Patent Application 81459, filed Feb. 2, 1987, and the later Chadwick et al U.S. Pat. No. 4,877,326 filed Feb. 19, 1988. The foregoing systems are designed to provide a "full sky" of illumination over essentially a linear field-of-view; i.e., one dimension of the field is much longer than the other.

In such linearly symmetric illumination systems, the illumination is substantially uniform along the longitudinal axis of the line of sensor elements, and also along the line perpendicular to the longitudinal axis. However, the uniformity drops significantly between these two lines, particularly along lines at 45° from these two lines. Thus, while the linearly symmetric illumination in the existing inspection systems is quite satisfactory for systems with resolution elements, e.g., pixels, of 5-6 microns, they are less than satisfactory with respect to higher resolution inspection systems, e.g., having pixels of about 0.5 microns.

OBJECTS AND SUMMARY OF THE INVENTION

An object of the present invention is to provide inspection apparatus for optically inspecting surfaces of workpieces including an improved illumination system, and particularly one which may be used with high resolution inspection apparatus, e.g., having resolution elements (pixels) in the order of 0.5 microns.

According to one aspect of the present invention, there is provided inspection apparatus of the type described above, but characterized in that the illumination system illuminates an area of the workpiece surface with a sky of illumination which is, with respect to each point in the illuminated area, substantially circularly symmetric over a solid angle around the optical axis passing perpendicularly through the optical sensor and the workpiece surface.

That is, the novel system is "circularly-symmetric", rather than "linearly-symmetric" according to the prior art. The differences between the "circularly-symmetric" illumination of the present invention, and the "linearly-symmetric" illumination of the prior art are more particularly described below together with the advantages provided by the "circularly-symmetric" system particularly when applied to inspection apparatus.

According to further features in the preferred embodiment of the invention described below, the illumination system comprises first light producing means producing, within said sky of illumination, a brightfield component of substantially circular configuration and uniform intensity; and second light producing means producing, within said sky of illumination, a darkfield component of substantially annular configuration and uniform intensity around the brightfield component. The illumination system further includes separate controls for the first and second light producing means for individually controlling their respective intensities.

According to further features in the described preferred embodiment, the second light producing means comprises a plurality of light sources arranged in an equally-spaced circular array around the optical axis and effective to substantially focus the light from the plurality of light sources on the workpiece surface. More particularly, the plurality of light sources include elliptical reflectors having their axes spaced equally around the optical axis. In the described preferred embodiment, there are eight such light sources and elliptical reflectors spaced every 45° around the optical axis. It is contemplated, however, that a different number of light sources may be used (e.g., sixteen), or even a single torroidal light source, or that refractors (lenses) may be used instead of reflectors.

According to another aspect of the present invention, there is provided an illumination system for illuminating a surface, characterized in that the illumination system produces a sky of illumination which is, with respect to each point in the illuminated surface, substantially circularly symmetric over a solid angle around the optical axis passing perpendicularly through the illuminated surface. More particularly, the illumination system comprises: first light producing means producing, within the sky of illumination, a brightfield component of substantially circular configuration and uniform intensity; and second light producing means producing, within the sky of illumination, a darkfield component of substantially annular configuration and uniform intensity around the brightfield component. The second light producing means includes a plurality of light sources arranged in an equally spaced circular array around the optical axis and are effective to substantially focus the light from the plurality of light sources on the workpiece surfaces.

Further features and the advantages of the invention will be apparent from the description below.

BRIEF DESCRIPTION OF THE DRAWINGS

The invention is herein described, by way of example only, with reference to the accompanying drawings, wherein.

DESCRIPTION OF A PREFERRED EMBODIMENT

Figure 1:
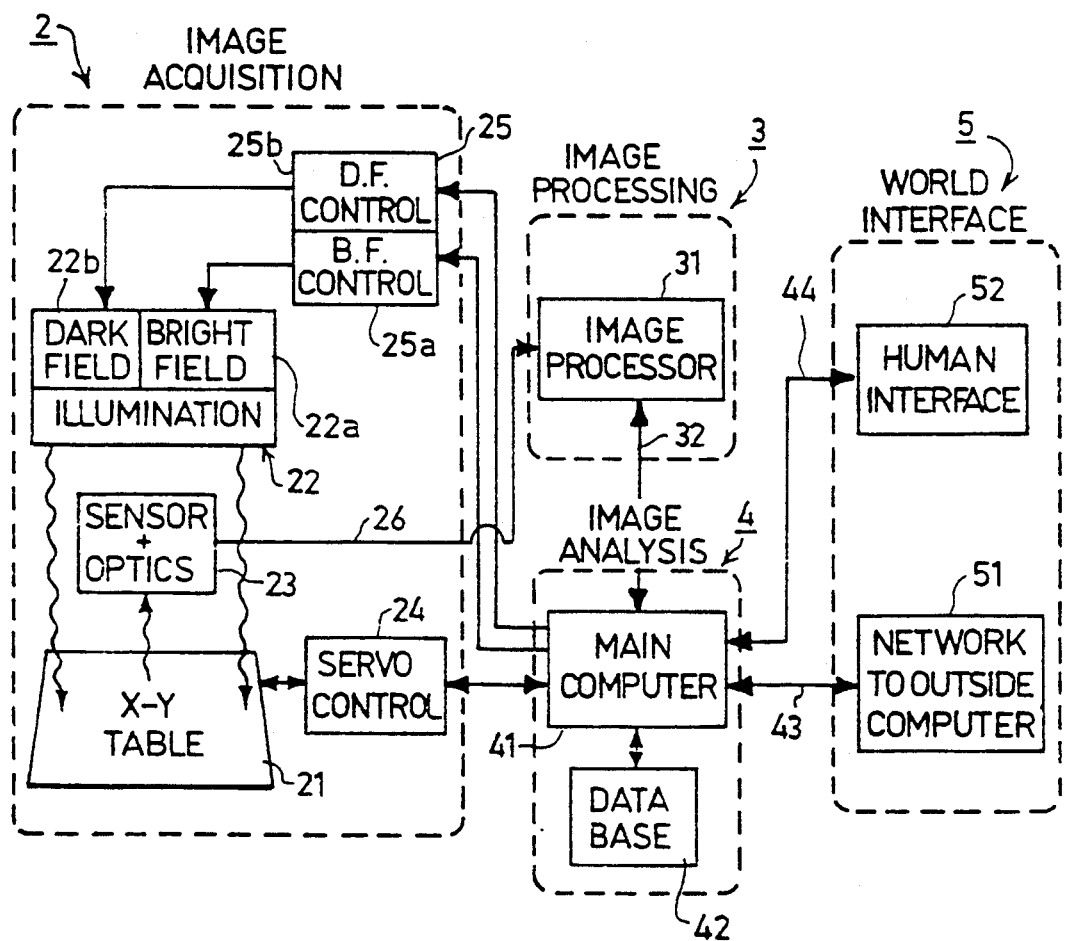
FIG. 1 is a block diagram illustrating one form of inspection apparatus constructed in accordance with the present invention for optically inspecting the surface of a workpiece, particularly a printed circuit board or wafer.

The overall automatic inspection system illustrated in FIG. 1 is intended for optically inspecting the surface of printed circuit boards, wafers, or like devices in order to detect flaws in the surface. The system includes the following subsystems: an image acquisition subsystem, generally designated 2; an image processing subsystem, generally designated 3; an image analysis subsystem, generally designated 4; and a world interface subsystem, generally designated 5.

The function of the image acquisition subsystem 2 is to illuminate and scan the workpiece, and to transfer an image of the scanned part to the image processing subsystem 3. Thus, the image acquisition subsystem 2 includes an X-Y table 21 adapted to receive the workpiece to be inspected; an illumination unit 22 for illuminating the workpiece on the table 21; a sensor/optical unit 23 for scanning the illuminated workpiece and for optically sensing its image; and a servo-control unit 24 for moving table 21 along one orthogonal axis and the sensor/optical unit 23 along the other orthogonal axis in order to sense the complete surface of the workpiece.

The illumination unit 22 includes a brightfield light producing means 22a, and a darkfield light producing means 22b. A control unit, generally designated 25, includes a brightfield control 25a for controlling the intensity of the brightfield illumination, and a darkfield control 25b for controlling the intensity of the darkfield illumination.

The output from the sensor/optical unit 23 of the image acquisition system 2, appears on output line 26 applied to the image processing subsystem 3.

The image processing subsystem 3 includes an image processor 31, whose function is to process the image and to segment it reliably into functional areas. Thus, when the workpiece is a printed circuit board, image processor 31 segments the output, appearing on line 26 from the image acquisition subsystem 2, into the functional areas of conductors and dielectric substrate. Image processor 31 is a special purpose hardware with dedicated software aimed at enhancing the image and segmenting it into its functional areas. The output from image processor 31 is applied via bus 32 to the image analysis subsystem 4.

The function of the image analysis subsystem 4 is to find all flaws in the segmented image, based on various algorithms. Thus, it includes a main computer 41 having logic circuitry for analyzing the electric signals outputted by the image processor 31, and for comparing them with the data stored in the memory of the database unit 42 for providing an indication of any discrepancies resulting from a defect in the inspected workpiece surface. The main computer 41 implements the flaw detection and flaw reporting algorithms, and effects the comparison with the reference images stored in the database 42 in order to determine whether a flaw exists, and if so, to indicate its location and thereby to enable the workpiece to be reworked to correct the flaw. As indicated earlier, the database 42 may store image data and/or design rules with respect to which the sensed workpiece data are to be compared.

The main computer 41 in the image analysis subsystem 4 also controls the brightfield control unit 25a, the darkfield control unit 25b, the servo-control unit 24, and the image processor 31. Its output is fed to the world interface subunit 5 via buses 43, and 44.

The output bus 43 from the image analysis subsystem 4 is applied to a network unit 51 in the world interface subsystem 5. Network unit 51 is a package of hardware and software allowing communication with outside computers. The world interface subsystem 5 further includes a human interface unit 52, e.g., monitor, permitting the operator to monitor the data outputted from the main computer, a keyboard, and/or other input device permitting intervention by the operator.

Except for the illumination unit 22 in the image acquisition subsystem 2 of FIG. 1, the overall system illustrated in FIG. 1 is well known and in commercial use, and therefore further details of the construction and operation of the system are not setforth herein. The remainder of the description will accordingly be restricted to a description of the illumination unit 22, as more particularly illustrated in FIGS. 2-6.

Figure 5:
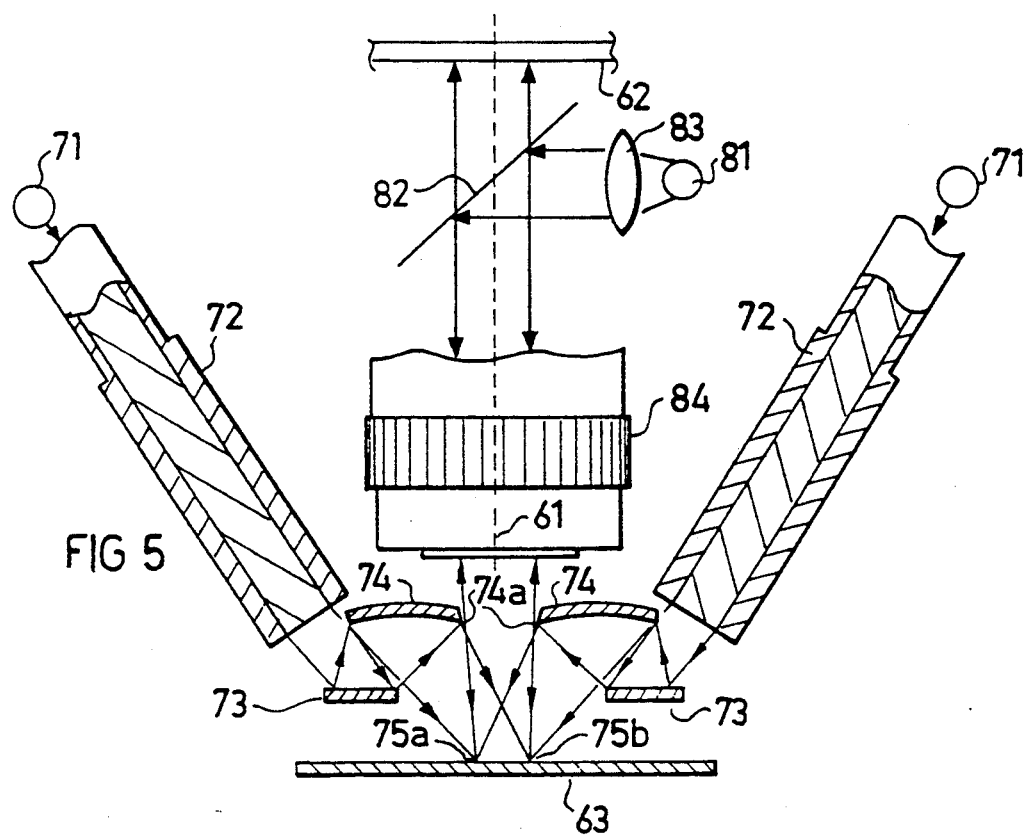
FIG. 5 is an optical diagram illustrating the operation of the illumination system of FIG. 2.

The construction and operation of the illumination unit 22 will be better understood by first referring to the optical diagram of FIG. 5. The function of illumination unit 22 is to illuminate an area of the workpiece surface with a sky of illumination which is, with respect to each point in the illuminated area, substantially circularly symmetric over a solid angle around the optical axis, indicated at 61 in FIG. 5, passing perpendicularly through the optical sensor 62 and the workpiece surface 63 to be inspected. This sky of illumination includes a brightfield component, shown as $S_B$ in FIG. 7b, of substantially circular configuration and of substantially uniform intensity, and a darkfield component, shown at $S_D$ in FIG. 7b, which is of substantially annular configuration and of substantially uniform intensity around the brightfield component $S_B$.

The relative intensities of the brightfield component $S_B$ and darkfield component $S_D$ are individually controlled by their respective control units 25a, 25b (FIG. 1), so that each such component may be individually varied as desired for any particular application. Thus, for many applications, the central, circular brightfield component of the sky of illumination would be adjusted to be of equal intensity to the annular darkfield component, but there are applications where the central brightfield component would be adjusted to be of lower intensity, and sometimes even of zero intensity.

Figure 6:
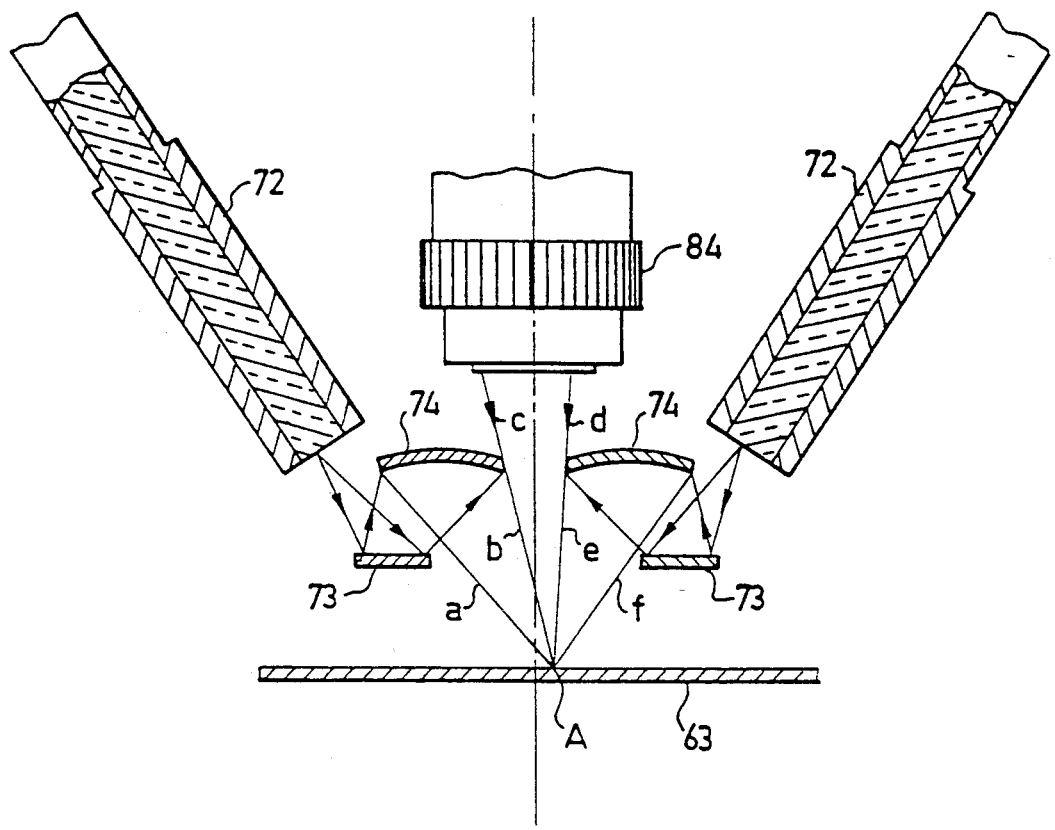
FIG. 6 is an optical diagram illustrating the light paths of marginal rays in the optical diagram of FIG. 5.

FIG. 6 illustrates the light paths of marginal rays impinging at any arbitrary point "A" within the field-of-view of the illumination system: rays a, b, e and f are marginal rays of the darkfield illumination, and rays c and d are marginal rays of the brightfield illumination. As is clearly seen in FIG. 6, each point within the effective field-of-view of the system is illuminated by both brightfield and darkfield components.

Since the optical diagram of FIG. 6 generally applies to any plane containing the optical axis, the resulting effect, as seen to an observer standing at point A and looking upwards, is a substantially circularly symmetric "sky" of illumination with respect to the optical axis. The "sky" observed from point A, as shown in FIG. 7b, is composed of a central circular component $S_B$, corresponding to the brightfield illumination, and an annular component $S_D$ surrounding the brightfield component and corresponding to darkfield illumination.

It is to be particularly noted that the effective field-of-view of the illumination system 22, defined as the area in workpiece surface 63 illuminated by a substantially circularly symmetric "sky", is substantially a circularly symmetrical area around the optical axis 61. That is, the "sky" of illumination is, with respect to each point in the illuminated area, substantially circularly symmetric over a solid angle around the optical axis 61 passing perpendicularly through the optical sensor and the workpiece surface.

Also, the circular symmetry arrangement illustrated in FIG. 6 renders the illumination system applicable to a scanner based on area sensors (e.g., a video camera), and is not limited to operation with line sensors, because of the described circular symmetry.

Figure 7A:
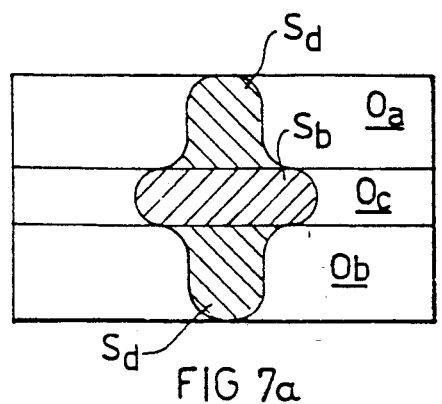
FIG. 7a illustrates the sky of illumination as observed from any point on the illuminated surface when illuminated by a "linearly-symmetric" system according to the prior art.
Figure 7B:
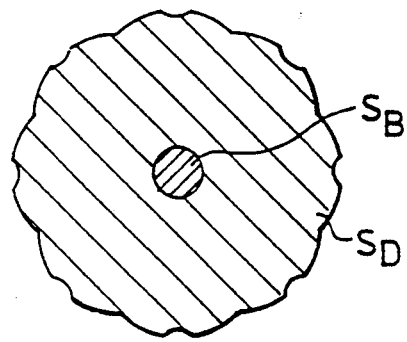
FIG. 7b illustrates the sky of illumination as observed from any point on the illuminated surface when illuminated by a "circularly-symmetric" system as described in FIGS. 2-6 of the present application.

The illumination system illustrated in FIGS. 5, 6 and 7b is to be contrasted with the prior art systems referred to earlier producing a full sky of illumination over essentially a linear field-of-view, in which one dimension of the field is much longer than the other. Moreover, the "sky" of illumination produced by such systems is also non-circularly symmetric. Thus, FIG. 7a illustrates the general appearance of the sky of illumination presented to an observer standing inside the illuminated linear field, in which it will be seen that the system is not circularly symmetric, but rather has two mutually perpendicular axes of symmetry. Such prior art systems are intended for use with linear sensors, and employ cylindrical optics for focusing the light.

Thus, in such prior art illumination system as illustrated by FIG. 7a, optical elements Oa and Ob are cylinder concentrators which give rise to illumination sky regions Sd, on opposite sides of the central sky region Sb. optical element Oc in FIG. 7a is typically a beam splitter, and its contribution to the illuminated sky is denoted as region Sb in FIG. 7a. Such prior art systems therefore do not allow a separate control of the brightfield and darkfield components. For example, region Sb in FIG. 7a contains not only the entire brightfield illumination, but also a substantial part of the darkfield illumination as well.

Figure 2:
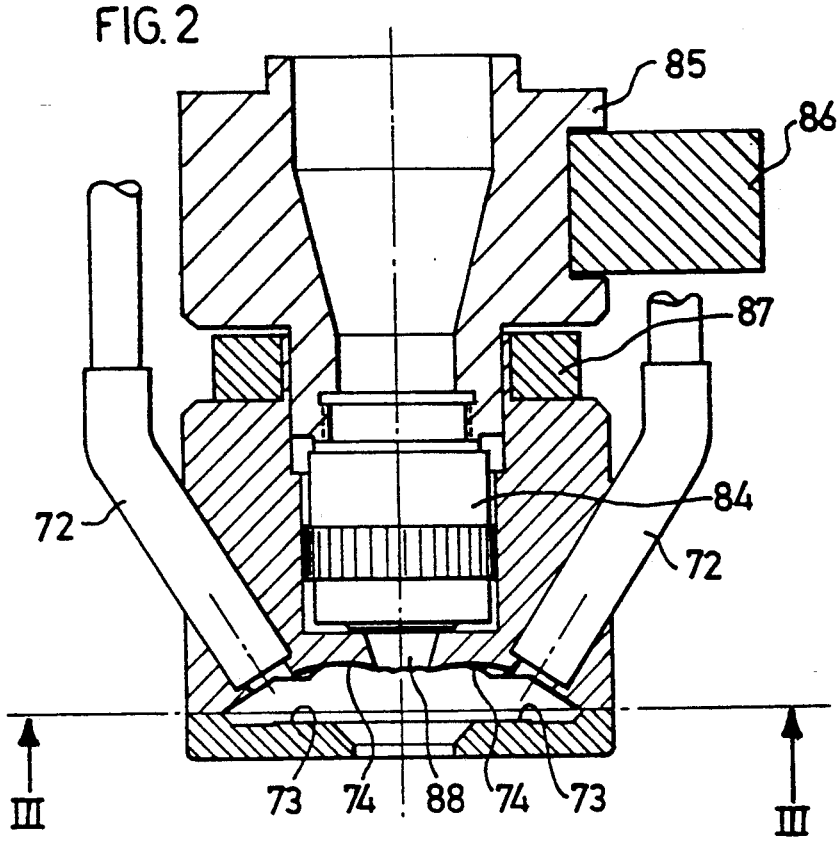
FIG. 2 more particularly illustrates the construction of the illumination system in the inspection apparatus of FIG. 1.
Figure 3:
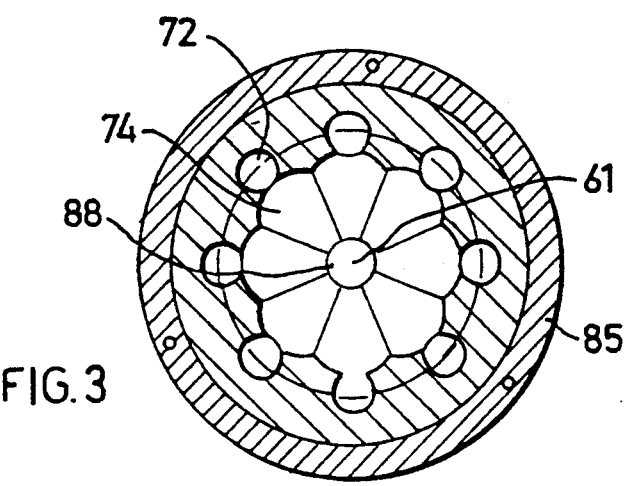
FIG. 3 is a sectional view along line III—III of FIG. 2.
Figure 4:
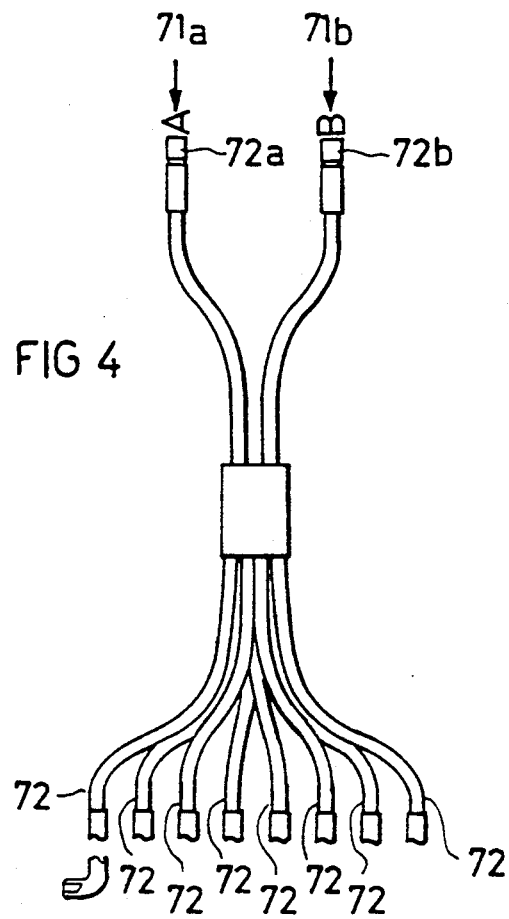
FIG. 4 illustrates the fiber optical light guide used for producing the darkfield illumination in the illumination system of FIG. 2.

FIGS. 2–4 more particularly illustrate one construction of an illumination system in accordance with the present invention which illuminates the workpiece surface with a circularly-symmetric sky of illumination, i.e., with a sky of illumination which is, with respect to each point in the illuminated area, substantially circularly symmetric over a solid angle around the optical axis passing perpendicularly through the optical sensor to the workpiece surface.

Thus, the darkfield illumination unit 22b includes one or more lamps 71, a plurality (preferably eight) of fiber optical light guides 72, a planar folding reflector 73 for each light guide, and an elliptical reflector 74 for each light guide. As shown particularly in FIG. 3, the eight elliptical reflectors 74 are disposed in a circular array around the optical axis 61, with the axes of the elliptical reflectors spaced every 45° around the optical axis. The eight elliptical reflectors 74 are designed to focus the light from the lamp (lamps) 71 passing through the eight fiber optical light guides 72 and reflected by the planar reflectors 73, to produce the annular darkfield component of the sky observed by each point in the illuminated field.

Each of the eight elliptical reflectors 74 is formed with an inner knife edge 74a (FIG. 5) to produce a sharp inner edge of the annular darkfield component of the sky over the illuminated area of the workpiece. That is to say, the points 74a in FIG. 5 define the outer circular edge of the brightfield component $S_B$ (FIG. 7b) of the sky of illumination observed at any point within the illuminated field of the workpiece surface; this brightfield component is contributed by the brightfield unit 22a (FIG. 1) and can be adjusted according to any desired intensity by the brightfield control 25a.

As shown in FIG. 5, the brightfield illumination unit 22a includes a lamp 81 mounted off-axis with respect to the optical axis 61 through the sensor 62. The brightfield illuminating unit 22a further includes a beam splitter 82 at the optical axis 61 and effective to reflect the light from lamp 81 to the workpiece surface 63, and also to transmit the light reflected from the workpiece surface to the sensor 62. The brightfield illumination unit 22a further includes a condensing lens 83 effective to direct the light from lamp 81, via the objective 84, onto the workpiece surface 63. Lens 83 may be a focusing lens effective to focus the light from lamp 81 onto the workpiece surface 63, but the brightfield illumination system may also be of the non-focusing type in order to somewhat blur the image of the source of light (e.g., a filament) from lamp 81 as received on the workpiece surface.

It will thus be seen that an observer at any point on the illuminated area of the workpiece sees an illuminated sky having a central brightfield component produced by light source 81, condensing lens 83, and beam splitter 82, and an annular darkfield component produced by the two lamps 71, the eight optical fiber light guides 72, their plane reflectors 73, and the eight elliptical reflectors 74. It will also be seen that the illuminated sky, including the central brightfield component and the annular darkfield component, is circularly symmetric over a solid angle with respect to the optical axis passing perpendicularly through the optical sensor 62 and the workpiece surface 63.

It will be further seen that the brightfield and darkfield components may be separately adjusted in intensity by the brightfield control unit 25a and darkfield control unit 25b, respectively; thus, both components of the illuminated sky may be adjusted to be exactly of the same intensity, or of different intensities (from zero to the maximum) as may be required for any particular application.

The illustrated arrangement, including the planar reflectors 73, provides additional advantages. Thus, these planar reflectors 73 serve as folding reflectors to decrease the distance required between the objective lens 84 and the workpiece surface 63. In addition, they enable the eight fiber optical light guides to be located above and around the objective lens 84. Such an arrangement permits the objective lens to be more closely located with respect to the workpiece, thereby greatly simplifying the lens design and effecting substantial savings in the light and power requirements in order to obtain the necessary signal-to-noise ratio for any scanning speed.

FIGS. 2-4 illustrate an example of a construction of a darkfield illumination system 22b in accordance with the optical diagram of FIG. 5. Thus, the objective lens 84 is mounted within a lens housing 85 having a pair of supports 86, 87. The lens housing 85 is formed with a circular array of eight bores for receiving the eight fiber optical light guides 72; and the inner surface of the housing carries, or is formed with, the eight elliptical reflectors 74 disposed in a circular array around the optical axis 61 through the central opening 88 of the housing. The eight planar reflectors 73 are formed in, or are carried by, a plate fixed to the end of housing 85 and having central opening 88 coaxial with the optical axis 61 for the uniform illumination produced by the illumination system.

As shown particularly in FIG. 3, the eight elliptical reflectors 74, together with the output ends of the respective fiber optical light guides 72 and respective planar reflectors 73, are arranged in a circular array around the optical axis 61, with the axes of the elliptical reflectors spaced every 45° around the optical axis as described earlier. Such a construction produces a substantially uniform darkfield component of sky illumination having an annular configuration and circularly symmetric with respect to the optical axis. This annular darkfield component of sky illumination surrounds the brightfield component of sky illumination produced by the brightfield illumination system 22a (elements 81-84, FIG. 5). The mirrors are preferably fabricated using diamond-turning technology.

FIG. 4 illustrates, for purposes of example, the construction of a fiber optical light guide which may be used for light guides 72 in FIGS. 2, 3 and 5. In this construction, two input lamps, shown at 71a, 71b, are used and are located adjacent to the two input ends 72a, 72b of the light guide. The input ends of the light guide are divided into the eight output ends 72 as shown in FIGS. 2, 3 and 5. For this purpose, the sum of the cross-sectional areas of the input ends 72a, 72b should approximately equal the sum of the cross-sectional areas of the eight output ends.

The circularly-symmetric illumination system illustrated in FIGS. 2-6 may be used for illuminating the workpiece surface with sky illumination which, as observed from each point of the illuminated field on the workpiece, is substantially uniform and substantially circularly symmetric over a solid angle of at least 60°, and up to about 110°, and which forms a light spot of about 2.6 mm on the workpiece surface. Such an illumination system has been found to be highly effective with high-resolution inspection apparatus having resolution elements (e.g., pixels) of about 0.5 microns. The described circularly-symmetric illumination system is to be compared to the existing linearly-symmetric illumination systems which are generally incapable of utilizing pixels, or other resolution elements, smaller than about 5-6 microns.

While the invention has been described above with respect to one preferred embodiment, it will be appreciated that this is set forth merely for purposes of example, and that many variations (some of which have been mentioned earlier), modifications and other applications may be made.

What is claimed is:

1. Inspection apparatus for optically inspecting the surface of a workpiece, comprising:

a memory for storing data relating to the desired features of the workpiece surface;

an illumination system for illuminating an area of the workpiece surface;

an electro-optical sensor for sensing the light reflected from the illuminated workpiece surface, and for outputting electric signals corresponding thereto;

and a processor including logic circuitry for analyzing the electric signals outputted by said electro-optical sensor, for comparing them with the data stored in said memory, and for providing an indication of any discrepancies with respect thereto indicating a defect in the inspected workpiece surface;

characterized in that said illumination system illuminates an area of the workpiece surface with a sky of illumination which is, with respect to each point in the illuminated area, substantially uniform and circularly symmetric over a solid angle around the optical axis passing perpendicularly through the electro-optical sensor and the workpiece surface; said illumination system comprising:

first light producing means producing, within said sky of illumination, a brightfield component of substantially circular configuration and uniform integrity;

and second light producing means producing, within said sky of illumination, a darkfield component of substantially annular configuration and uniform intensity around said brightfield component;

said second light producing means including a plurality of light sources arranged in an equally spaced circular array around said optical axis and a plurality of reflectors effective to substantially focus the light from said plurality of light sources on the workpiece surfaces, each of said reflectors being formed with an inner knife edge to produce a sharp inner edge of the annular darkfield component of the sky of illumination.

2. The apparatus according to claim 1, wherein said illumination system further includes separate controls for said first and second light producing means for individually controlling their respective intensities.

3. The apparatus according to claim 1, wherein said plurality of reflectors are elliptical reflectors having their axes spaced equally around said optical axis.

4. The apparatus according to claim 3, wherein there are eight of said light sources and elliptical reflectors spaced every 45° around said optical axis.

5. The apparatus according to claim 3, wherein said second light producing means further includes a folding planar reflector between each of the light sources and its respective elliptical reflector.

6. The apparatus according to claim 1, wherein said second light producing means further includes a fiber optical light guide for each of said light sources.

7. The apparatus according to claim 6, wherein said second light producing means includes two input lamps for illuminating the fiber optical light guides of said light sources.

8. The apparatus according to claim 1, wherein said first light producing means comprises:
an input lamp off-axis with respect to said optical axis through said sensor;
and a beam splitter at said optical axis for reflecting the light from said off-axis lamp to said workpiece surface, and for transmitting the light reflected from said workpiece surface to said optical sensor.

9. The apparatus according to claim 1, wherein said optical sensor includes a linear array of high resolution pixels.

10. An illumination system for illuminating a surface, characterized in that said illumination system produces a sky of illumination which is, with respect to each point in the illuminated surface, substantially uniform and circularly symmetric over a solid angle around the optical axis passing perpendicularly through the illuminated surface; said illumination system comprising:
first light producing means producing, within said sky of illumination, a brightfield component of substantially circular configuration and uniform intensity;
and second light producing means producing, within said sky of illumination, a darkfield component of substantially annular configuration and uniform intensity around said brightfield component;
said second light producing means including a plurality of light sources arranged in an equally spaced circular array around said optical axis and a plurality of reflectors effective to substantially focus the light from said plurality of light sources on the workpiece surfaces, each of said reflectors being formed with an inner knife edge to produce a sharp inner edge of the annular darkfield component of the sky of illumination.

11. The illumination system according to claim 10, wherein said illumination system further includes separate controls for said first and second light producing means for individually controlling their respective intensities.

12. The illumination system according to claim 10, wherein said plurality of reflectors are elliptical reflectors having their axes spaced equally around said optical axis.

13. The illumination system according to claim 12, wherein there are eight of said light sources and elliptic reflectors spaced every 45° around said optical axis.

14. The illumination system according to claim 12, wherein said second light producing means further includes a folding planar reflector between each of the light sources and its respective elliptical reflector.

15. The illumination system according to claim 10, wherein said second light producing means includes a fiber optical light guide for each of said light sources.

16. The illumination system according to claim 15, wherein said second light producing means includes two input lamps for illuminating the fiber optical light guides of said eight light sources.

17. The illumination system according to claim 10, wherein said first light producing means comprises:
an input lamp off-axis with respect to said optical axis through said sensor; and
a beam splitter at said optical axis for reflecting the light from said off-axis lamp to said workpiece surface, and for transmitting the light reflected from said workpiece surface to said optical sensor.

18. The illumination system according to claim 10, further including an optical sensor comprising a linear array of high resolution pixels for sensing the light reflected from the illuminated surface.

* * * * *